United States Patent
Bezanson et al.

(10) Patent No.: US 10,149,660 B2
(45) Date of Patent: Dec. 11, 2018

(54) ULTRASOUND ENDOSCOPE AND METHODS OF MANUFACTURE THEREOF

(71) Applicant: DALHOUSIE UNIVERSITY, Halifax (CA)

(72) Inventors: Andre B. Bezanson, Halifax (CA); Robert B. A. Adamson, Halifax (CA); Jeremy A. Brown, Halifax (CA)

(73) Assignee: DALHOUSIE UNIVERSITY, Halifax, NS (CA)

( * ) Notice: Subject to any disclaimer, the term of this patent is extended or adjusted under 35 U.S.C. 154(b) by 804 days.

(21) Appl. No.: 14/420,452

(22) PCT Filed: Aug. 9, 2013

(86) PCT No.: PCT/CA2013/050613
§ 371 (c)(1),
(2) Date: Feb. 9, 2015

(87) PCT Pub. No.: WO2014/022938
PCT Pub. Date: Feb. 13, 2014

(65) Prior Publication Data
US 2015/0209005 A1 Jul. 30, 2015

Related U.S. Application Data

(60) Provisional application No. 61/681,320, filed on Aug. 9, 2012, provisional application No. 61/710,696, filed on Oct. 6, 2012.

(51) Int. Cl.
*H01L 41/09* (2006.01)
*A61B 8/12* (2006.01)
(Continued)

(52) U.S. Cl.
CPC .............. *A61B 8/12* (2013.01); *A61B 8/4488* (2013.01); *H05K 1/189* (2013.01); *H05K 3/403* (2013.01);
(Continued)

(58) Field of Classification Search
CPC ................................ A61B 8/12; A61B 8/4488
(Continued)

(56) References Cited

U.S. PATENT DOCUMENTS 5,427,106 A * 6/1995 Breimesser ............ H04R 17/00
310/326
5,559,388 A * 9/1996 Lorraine ............... B06B 1/0622
310/327
(Continued)

FOREIGN PATENT DOCUMENTS

JP 2002247696 8/2002
WO 2012075153 6/2012

OTHER PUBLICATIONS

Bezanson, A.; Adamson, R.; Brown, J.A., "Fabrication and performance of a miniaturized 64-element high-frequency endoscopic phased array," Ultrasonics, Ferroelectrics, and Frequency Control, IEEE Transactions on , vol. 61, No. 1, pp. 33,43, Jan. 2014.
(Continued)

*Primary Examiner* — Thomas Dougherty
(74) *Attorney, Agent, or Firm* — Hill & Schumacher (57) ABSTRACT

To address limitations of conventional transducers, a phased array transducer is provided with a form factor suitable o for packaging into, e.g., an endoscope. A method of manufacture of small packaging transducers is also provided, whereby the overall package size is reduced by electrically connecting signal wires to array electrodes at an angle approximately normal to the array surface, thus largely
(Continued)

11 Claims, 5 Drawing Sheets

(51) Int. Cl.
 *A61B 8/00* (2006.01)
 *H05K 1/18* (2006.01)
 *H05K 3/40* (2006.01)
 *H05K 3/00* (2006.01)
(52) U.S. Cl.
 CPC ..... *H05K 3/0052* (2013.01); *H05K 2203/049* (2013.01); *Y10T 29/49151* (2015.01); *Y10T 29/49165* (2015.01)
(58) Field of Classification Search
 USPC ...................................................... 310/334
 See application file for complete search history.

(56) References Cited

U.S. PATENT DOCUMENTS

| | | | | |
|---|---|---|---|---|
| 5,810,009 | A * | 9/1998 | Mine ..................... | B06B 1/0622 310/334 |
| 5,857,974 | A * | 1/1999 | Eberle .................. | A61B 1/0011 29/25.35 |
| 6,043,590 | A * | 3/2000 | Gilmore ................ | B06B 1/0607 310/334 |
| 6,153,967 | A * | 11/2000 | Kobayashi ............ | B06B 1/0622 310/327 |
| 6,541,896 | B1 | 4/2003 | Piel, Jr. et al. | |
| 7,745,976 | B2 * | 6/2010 | Cerofolini ............. | A61B 8/00 310/334 |
| 7,795,784 | B2 * | 9/2010 | Davidsen .............. | B06B 1/0622 310/334 |
| 8,189,342 | B2 | 5/2012 | Bang et al. | |
| 8,803,404 | B2 * | 8/2014 | Kwon ................... | B06B 1/0622 29/594 |
| 2004/0095045 | A1 | 5/2004 | Baumgartner | |
| 2007/0047377 | A1 | 3/2007 | Bang et al. | |
| 2007/0222339 | A1 | 9/2007 | Lukaes et al. | |
| 2008/0002375 | A1* | 1/2008 | Nozaki ................. | H05K 1/0266 361/749 |
| 2009/0034370 | A1* | 2/2009 | Guo ...................... | B06B 1/0622 367/180 |
| 2009/0221873 | A1 | 9/2009 | McGrath | |
| 2013/0100775 | A1* | 4/2013 | Spigelmyer ........... | B06B 1/0607 367/137 |
| 2014/0350407 | A1* | 11/2014 | Chaggares ............ | B06B 1/0622 600/459 |

OTHER PUBLICATIONS

Latham, K.; Arthur, C.; Brown, J. "Broad-band, large delay range, high precision, and variable analog delay lines for a high-frequency phased array beamformer", Ultrasonics Symposium (IUS), 2014 IEEE International, On pp. 2197-2200.
Bezanson, A.; Leadbetter, J.; Brown, J.A. "Fabrication of a high-frequency phased array with sparse Vernier array element spacing for grating lobe suppression", Ultrasonics Symposium (IUS), 2014 IEEE International, On pp. 671-674.
Bezanson, A.; Adamson, R.; Brown, J.A., "Fabrication and performance of a miniaturized 64-element high-frequency endoscopic phased array," Ultrasonics Symposium (IUS), 2013 IEEE International , vol., No., pp. 765,768, Jul. 21-25, 2013.
Brown, J.A.; Leadbetter, J.; Leung, M.; Bezanson, A.; Adamson, R., "A low cost open source high frame-rate high-frequency imaging system," Ultrasonics Symposium (IUS), 2013 IEEE International , vol., No., pp. 549,552, Jul. 21-25, 2013.
J. M. Cannata, J. A. Williams, Q. Zhou, T. A. Ritter, and K. K. Shung, "Development of a 35-MHz piezo-composite ultrasound array for medical imaging," IEEE Trans. Ultrason. Ferroelectr. Freq. Control, vol. 53, No. 1, pp. 224-236, 2006.
J. A. Brown, F. S. Foster, A. Needles, E. Cherin, and G. R. Lockwood, "Fabrication and performance of a 40-MHz linear array based on a 1-3 composite with geometric elevation focusing," IEEE Trans. Ultrason. Ferroelectr. Freq. Control, vol. 54, No. 9, pp. 1888-1894, 2007.
J. M. Cannata, J. A. Williams, and K. K. Shung, "A kerfless 30 MHz linear ultrasonic array," in Proc. IEEE Ultrasonics Symp., 2005, vol. 1, pp. 109-112.
H.-C. Yang, J. Cannata, J. Williams, and K. K. Shung, "Crosstalk reduction for high-frequency linear-array ultrasound transducers using 1-3 piezocomposites with pseudo-random pillars," IEEE Trans. Ultrason. Ferroelectr. Freq. Control, vol. 59, No. 10, pp. 2312-2321, 2012.
J. M. Cannata, J. A. Williams, C. H. Hu, and K. K. Shung, "Development of high frequency linear arrays using interdigital bonded composites," in in Proc. IEEE Ultrasonics Symp., 2008, pp. 686-689.
M. Lukacs, J. Yin, G. Pang, R. C. Garcia, E. Cherin, R. Williams, J. Mehi, and F. S. Foster, "Performance and characterization of new micromachined high-frequency linear arrays," IEEE Trans. Ultrason. Ferroelectr. Freq. Control, vol. 53, No. 10, pp. 1719-1729, 2006.
Q . Zhou, D. Wu, C. Liu, B. Zhu, F. Djuth, and K. K. Shung, "Micro-machined high-frequency (80 MHz) PZT thick film linear arrays," IEEE Trans. Ultrason. Ferroelectr. Freq. Control, vol. 57, No. 10, pp. 2213-2220, 2010.
F. S. Foster, J. Mehi, M. Lukacs, D. Hirson, C. White, C. Chaggares, and A. Needles, "A new 15-50 MHz array-based micro-ultrasound scanner for preclinical imaging," Ultrasound Med. Biol., vol. 35, No. 10, pp. 1700-1708, Oct. 2009.
C . Hu, L. Zhang, J. M. Cannata, and K. K. Shung, "Development of a digital high frequency ultrasound array imaging system," in Proc. IEEE Int. Ultrasonics Symp., 2010, pp. 1972-1975.
L . Sun, W. D. Richard, J. M. Cannata, C. C. Feng, J. A. Johnson, J. T. Yen, and K. K. Shung, "A high-frame rate high-frequency ultrasonic system for cardiac imaging in mice," IEEE Trans. Ultrason. Ferroelectr. Freq. Control, vol. 54, No. 8, pp. 1648-1655, 2007.
Z. Torbatian, R. Adamson, M. Bance, and J. A. Brown, "A splitaperture transmit beamforming technique with phase coherence grating lobe suppression," IEEE Trans. Ultrason. Ferroelectr. Freq. Control, vol. 57, No. 11, pp. 2588-2595, 2010.
X. C. Jin, B. T. Ehuri-Yakub, F. L. Degertekin, I. Ladabaum, and S. Calmes, "Micromachined capacitive ultrasonic immersion transducer for medical imaging," in Proc. 20th Annu. Int. Conf. IEEE Engineering in Medicine and Biology Society, 1998, vol. 2, pp. 779-782.
I. O. Wygant, D. T. Yeh, X. Zhuang, S. Vaithilingam, A. Nikoozadeh, O. Oralkan, A. Sanli Ergun, G. G. Yaralioglu, and B. T. Khuri-Yakub, "Integrated ultrasound imaging systems based on capacitive micromachined ultrasonic transducer arrays," in IEEE Sensors, 2005, p. 704-707.
T. Pedersen, T. Zawada, K. Hansen, R. Lou-Moeller, and E. V. Thomsen, "Fabrication of high-frequency pMUT arrays on silicon substrates," IEEE Trans. Ultrason. Ferroelectr. Freq. Control, vol. 57, No. 6, pp. 1470-1477, 2010.
D. T. Yeh, O. Oralkan, A. S. Ergun, X. Zhuang, I. O. Wygant, and B. T. Khuri-Yakub, "High-frequency CMUT arrays for highresolution medical imaging," in Medical Imaging, 2005, pp. 87-98.
K. Midtbo, A. Ronnekleiv, K. A. Ingebrigtsen, J. Due-Hansen, E. Poppe, D. T. Wang, G. U. Jensen, and K. Schjolberg-Henriksen, "High-frequency CMUT arrays with phase-steering for in vivo ultrasound imaging," in IEEE Sensors, 2012, pp. 1-5.
D. T. Yeh, O. Oralkan, I. O. Wygant, A. S. Ergun, J. Wong, and B. T. Khuri-Yakub, "High-resolution imaging with high-frequency 1-D linear CMUT arrays," in IEEE Int. Ultrasonics Symp., 2005, pp. 665-668.
M. Zipparo, C. Oakley, R. Denny, S. Azim, V. Balannik, Z. Soferman, M. Berman, R. Nechushtai, and D. Kopelman, "3-D laparoscopic imaging," in IEEE Ultrasonics Symp., 2008, pp. 40-44.

(56) References Cited

OTHER PUBLICATIONS

D. T. Yeh, O. Oralkan, I. O. Wygant, M. O'Donnell, and B. T. Khuri-Yakub, "3-D ultrasound imaging using a forward-looking CMUT ring array for intravascular/intracardiac applications," IEEE Trans. Ultrason. Ferroelectr. Freq. Control, vol. 53, No. 6, pp. 1202-1211, 2006.

Z. Wang, W. Zhu, H. Zhu, J. Miao, C. Chao, C. Zhao, and O. K. Tan, "Fabrication and characterization of piezoelectric micromachined ultrasonic transducers with thick composite PZT films," IEEE Trans. Ultrason. Ferroelectr. Freq. Control, vol. 52, No. 12, pp. 2289-2297, 2005.

U. Demirci, A. S. Ergun, O. Oralkan, M. Karaman, and B. T. Khuri-Yakub, "Forward-viewing CMUT arrays for medical imaging," IEEE Trans. Ultrason. Ferroelectr. Freq. Control, vol. 51, No. 7, pp. 886-894, 2004.

PCT/CA2013/050613 International Search reported dated Oct. 28, 2013.

PCT/CA2013/050613 Written Opinion dated Oct. 28, 2013.

\* cited by examiner

ULTRASOUND ENDOSCOPE AND METHODS OF MANUFACTURE THEREOF

CROSS-REFERENCE TO RELATED APPLICATIONS

This application is a National Phase application claiming the benefit of the international PCT Patent Application No. PCT/CA2013/050613, that claims the benefit of U.S. Provisional Patent Application Ser. No. 61/681,320, filed Aug. 9, 2012, in English, and of U.S. Provisional Patent Application Ser. No. 61/710,696, filed Oct. 6, 2012, in English; each of which is hereby incorporated by reference in its entirety.

BACKGROUND

Array-based endoscopic ultrasound systems operating at frequencies in the 1-10 MHz range are used frequently for laparoscopic imaging where they provide fast scanning rates, dynamic focusing and beam steering. For endoscopic imaging applications requiring higher resolution such as intravascular, intracardiac, transurethral, trans-nasal and transtympanic imaging, ultrasound arrays have been challenging to manufacture owing the small element size, small element pitch and need to package the finished endoscope into a small enough package to enter the required lumens. These applications have, therefore, been served mainly by single element ultrasound endoscopes which, compared to arrays, suffer slower frame rates, a tradeoff between depth of field and lateral resolution and the necessity of having moving parts in the endoscope head which adds bulk and causes unwanted vibrations.

In recent years there has been significant progress in developing fully sampled forward looking high frequency linear array transducers. For most applications a phase-array endoscope would offer significant improvements over a single-element endoscope. However, although the elements are conventionally proportioned in these arrays, the overall packaging of the transducers remains relatively large. This limits the application of the arrays to topical use where images are generated from outside the body.

SUMMARY

In general, in an aspect, an ultrasonic array has piezoelectric material and a plurality of electrodes. Each electrode is electrically connected to a respective signal wire, and the plurality of signal wires are embedded in a printed circuit board, the board having an angle of greater than about 60 degrees with respect to the array. In certain implementations, the configuration described above is included in an endoscope. The angle can be greater than 70 degrees. The angle can be greater than 80 degrees. The angle can be approximately 90 degrees. The printed circuit board can be a flexible circuit.

In general, in an aspect, a method of manufacture of any of the above includes creating vias in the printed circuit board and cutting the vias transversely to expose conductive material at the edge of the board. In certain implementations, the array is then wire bonded to the conductive material, such that the material acts as a wire bonding pad. Other implementations are possible, such as generally when the array is electrically connected to the conductive material by thin metal film, conductive epoxy, or the like. The cutting can be accomplished by a dicing saw or by similar methods. The cutting can be accomplished by a laser.

In general, in an aspect, an ultrasonic array has piezoelectric material and a plurality of electrodes. Each electrode is correspondingly electrically connected to one of a plurality of signal wires, the wires having an angle of greater than about 60 degrees with respect to the array. In certain implementations, the angle can be greater than 70 degrees. The angle can be greater than 80 degrees. The angle can be approximately 90 degrees.

In general, in an aspect, a method of manufacture of approximately perpendicular wire bonds includes creating vias in a flexible circuit and cutting the vias transversely to expose conductive material at the edge of the flexible circuit.

In general, in an aspect, a method of manufacture of electrical connections between an ultrasonic array and a printed circuit board includes creating vias in the board and cutting the vias transversely to expose the conductive material at the edge of the board.

These and other features and aspects, and combinations of them, may be expressed as methods, systems, components, means and steps for performing functions, business methods, program products, and in other ways.

Other advantages and features will become apparent from the following description and from the claims.

DESCRIPTION

PARTS LEGEND

100 Flex circuit, printed circuit board
102 Transducer stack, backing
104 Wire bonding pads
106 Wire to/from array element
108 Piezoelectric material
110 Electrodes
112 Array, ultrasonic array
120 Cut
122 Discarded half of the board edge
124 Exposed conductive material at the board edge
126 Via
128 Signal wire Miniaturized high-frequency, ultrasonic phased array endoscopes have been successfully designed and fabricated. An array with an electrical harness (such as flex or PCB or series of conductors) may be set a defined angle relative to a stack. There may be no bend required. The volumetric footprint can be minimized as well as the number of components.

Figure 1:
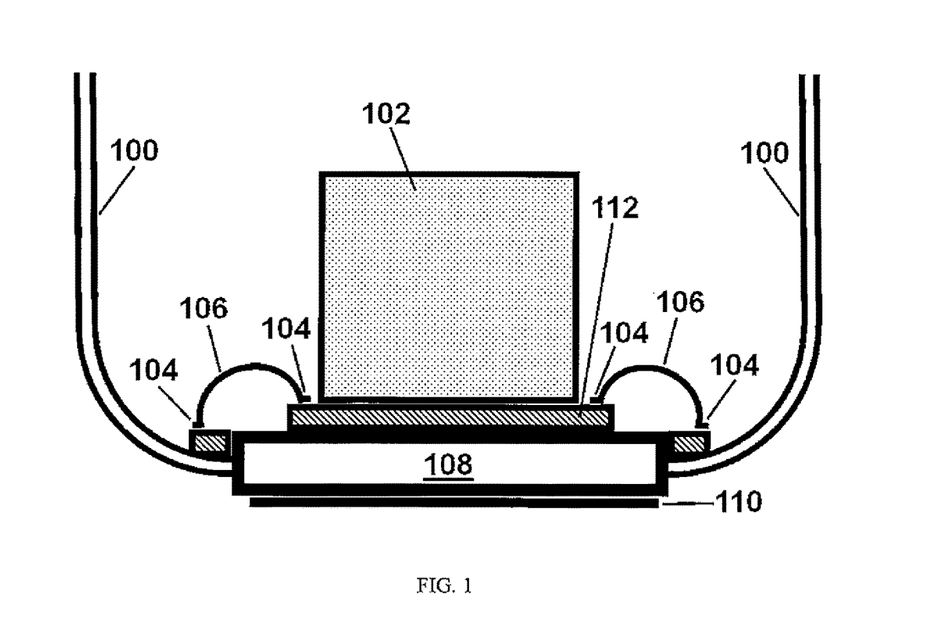
FIG. 1 shows a partial perspective view of the probe end of a conventional endoscope.

The advantages of an endoscope of this invention, as well as methods of manufacture of such endoscopes, can be seen by contrast to a conventional endoscope design in FIG. 1. At the probe end, a surface of piezoelectric material 108 is systematically electroded with electrodes 110, such that it defines an array 112 of individual elements that transmit and receive acoustic signals. Piezoelectric materials such as lead zirconate titanate (PZT) or lead manganese niobate in solid solution with lead titanate (PMNx-PT(1-x)) are often used.

To achieve additional separation between elements, in some cases kerfs (cuts made into the piezoelectric material 108) are made using a saw, laser, reactive ion etching or other methods. Each element in the array 112 is electrically connected (generally by way of a wire bonding pad) to a wire 106, which is correspondingly electrically connected on its other end by wire bonding pads 104 on a printed circuit board 100. Signal wires (not shown) embedded in the printed circuit board 100 are electrically connected to each pad 104, and send each signal from each element to the distal end of the probe (this is the end which is mechanically manipulated by a clinician). Often, the printed circuit board is a flexible (flex) circuit, which packages many of signal wires composed of conductive material by sandwiching them between flexible polymer layers. Printed circuit board 100 could also be inflexible, in which the insulating layers may be FR-4 fiberglass.

Note that in the conventional endoscope design of FIG. 1, a flex circuit 100 is approximately parallel to the surface of the array 112 for a significant distance before bending away from the probe end. The smallest dimension possible for such an endoscope is limited by how much of the flex circuit remains at the probe end. Typically, bonding pads 104 are exposed on both the flex circuit 100 and the array 112, and wires 106 are used to attach array pads and flex circuit pads to each other. In order to prevent damage to the flex circuit 100, the manufacturer specifies a minimum bend radius, often on the order of a few millimeters for a multilayer flex circuit such as those used to carry ultrasound array signals. This minimum bend radius requires that the flex circuit extend laterally from the ultrasound array for several millimeters before bending back, which greatly increases the cross-sectional area of the device. It is possible, in some embodiments, that no other structures are needed for mechanical support. In some embodiments, attachment may also be made to wires carried in another structure; if such structure is attached so that the wires meet the plane of the array surface, then a minimum bend radius may be required to avoid damaging such wires. Since the minimum size of a lumen into which the endoscope can enter is limited by the endoscope's cross-sectional area it is desirable to reduce the cross-sectional area as much as possible.

Figure 2:
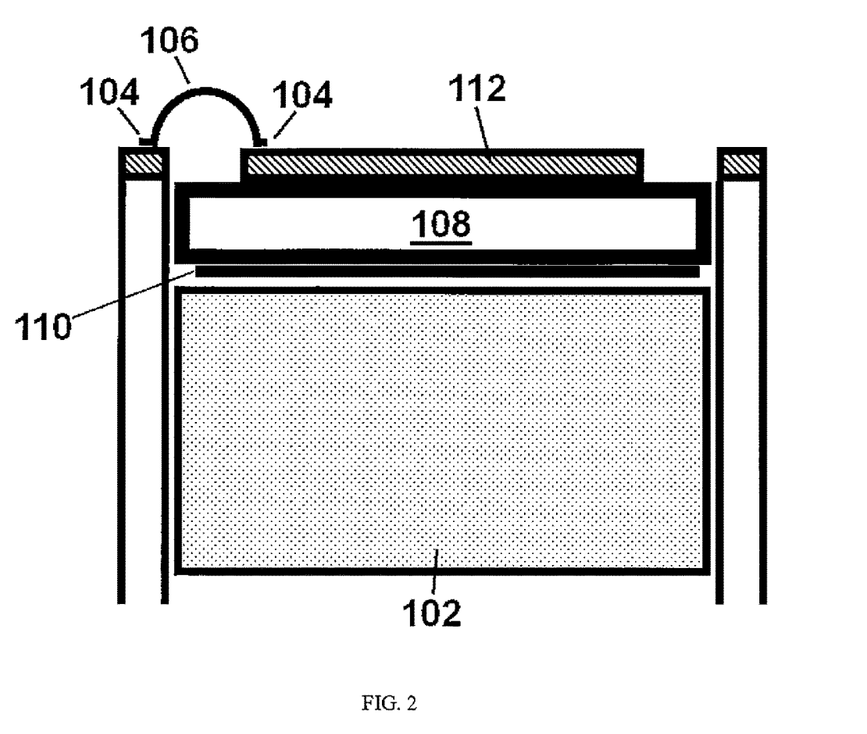
FIG. 2 shows a sectional view of the probe end of an endoscope of the present invention.
Figure 3:
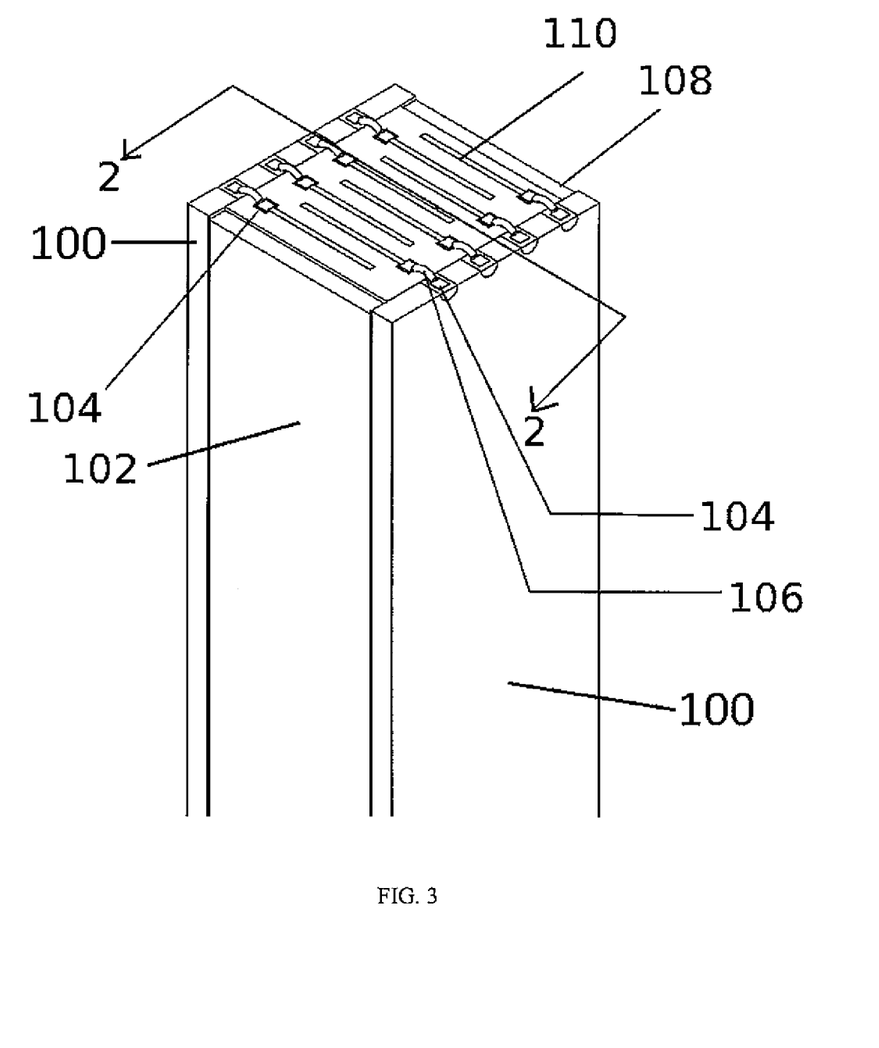
FIG. 3 shows a partial perspective view of the probe end of an endoscope of the present invention.

We now turn to an embodiment of the endoscope of the present invention; see FIGS. 2 and 3. Rather than have a printed circuit board 100 (such as a flex circuit) wire bonded approximately parallel to the surface of an array 112, instead the flex circuits are wire bonded (or otherwise electrically connected) approximately normal to the array surface. In such an arrangement the flex circuit does not bend, and the cross-sectional probe area need only be large enough to accommodate the array elements, bonding pads, and the thickness of the flex circuit at the probe end. This arrangement can be used in a variety of applications, including endoscopic high-frequency phased array ultrasound systems, non-endoscopic high-frequency ultrasound phased arrays, and both endoscopic and non-endoscopic phased and linear ultrasound arrays. In some embodiments, an endoscope of the present invention comprises a 40 MHz, 64-element phased array transducer packaged into a 2.47 mm by 2.42 mm endoscopic form factor, in which the array is a forward looking kerfless design based on PMN-32% PT with an element-to-element pitch of 38 microns. In some embodiments, the angle of the flex circuit with respect to the array is approximately 90 degrees. In some embodiments, the angle of the flex circuit with respect to the array is between 80 and 90 degrees. In some embodiments, the angle of the flex circuit with respect to the array is between 70 and 90 degrees. In some embodiments, the angle of the flex circuit with respect to the array is between about 60 and 90 degrees. In some embodiments crossing the normal plane, the angle of the flex circuit with respect to the array may exceed 90 degrees.

Attaching a printed circuit board approximately perpendicular to an array creates a manufacturing challenge because wire bonds between the array and the printed circuit board must connect to the board edge-on. In particular, flex circuitry is built by attaching together laminar layers, thus bonding pads cannot easily be mounted on the edge of a flex circuit. Moreover, because wire bonds are usually made between two parallel surfaces, it is difficult to make connections to bonding pads on the surface of a printed circuit board in this configuration, whether it is flexible or inflexible. The present invention solves these challenges by providing a novel method of manufacture. In some embodiments, this method enables wire bonding of signal wires to array elements; electrical connection is also possible using conductive epoxy or thin film metal deposition.

Figure 4:
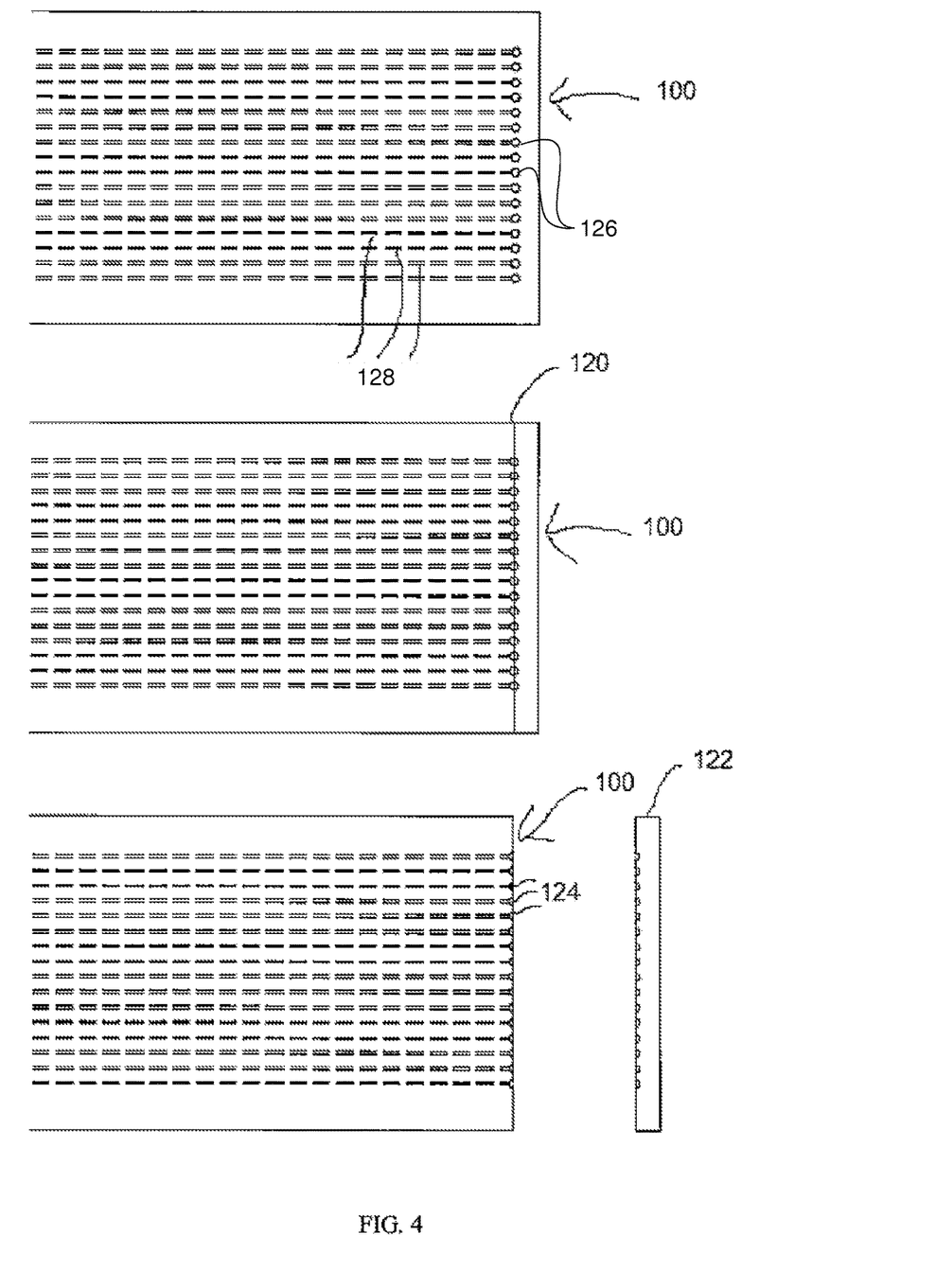
FIG. 4 depicts steps, from top to bottom, in the method of manufacture of the present invention.

In a wire bonding embodiment, the method of manufacture includes the following steps (see FIG. 4). A set of filled partial vias 126 is formed in the printed circuit board 100 (FIG. 4 top). These vias correspond to the position of the embedded signal wires 128, which are composed of conductive material suitable for electrical connections. In some embodiments, this procedure is performed twice such that the vias 126 are arranged in two rows through the depth of the printed circuit board 100, with one row through the top two layers and one through the bottom two layers such that they alternate. The board is then cut across its width with a dicing saw so as to cut the vias 126 in half near the edge of the board (FIG. 4 middle), exposing conductive material 124 corresponding to each signal wire at the site of the cut 120 (FIG. 4 bottom). The remainder 122 is discarded. In methods of manufacture of endoscopes of the present invention, wire bonds are then made between an array 112 and the cut vias 126 in the board, thus allowing a connection to be made without introducing any bending in the printed circuit board.

See below for an example of endoscopes of the present invention constructed using a method of manufacture of the present invention.

EXAMPLE

The array substrate was a 2.4 mm by 2.4 mm piece of PMN-32% PT lapped to 47 um thickness. An array of 64 electrodes was photolithographically defined on the top surface of this substrate with an electrode width of 27 um and an element-to-element pitch of 37 um. Each electrode was fanned out to a bonding pad arranged in two rows on each side of the array (four rows total). A 1.2 um layer of aluminum was sputtered onto the back side of the array to define a ground electrode, and a thick layer of conductive epoxy was attached to it to act as an absorbent acoustic backing layer. This epoxy was removed with a dicing saw in order to avoid making the bonding pads piezoelectrically active. Two 6-layer flex circuit boards were designed to connect to the elements from either side of the array. Each flex circuit had 32 traces terminating at individual copper-filled vias near the end of the board. The flex circuits were cut through the middle of the solid vias using a dicing saw. The two flex circuit boards were epoxied onto opposite sides of the transducer stack such that the diced vias were aligned with the bonding pads fanned out from the array. A jig was then machined to hold the flex+transducer stack upright in front of the wire-bonding tool. 15-micron thick aluminum wire bonds were used to connect the bonding pads on the array to the diced vias within the thickness of the array. The wirebonds were encapsulated with a thick insulating epoxy consisting of a 30% by volume mixture of Alumina powder and Epotek 301 (Epotek) insulating epoxy. A matching layer/lens combination was then epoxied onto the front face of the endoscope. Micro-coaxial cables were directly soldered to the flex circuit at the distal end of the probe.

Figure 5:
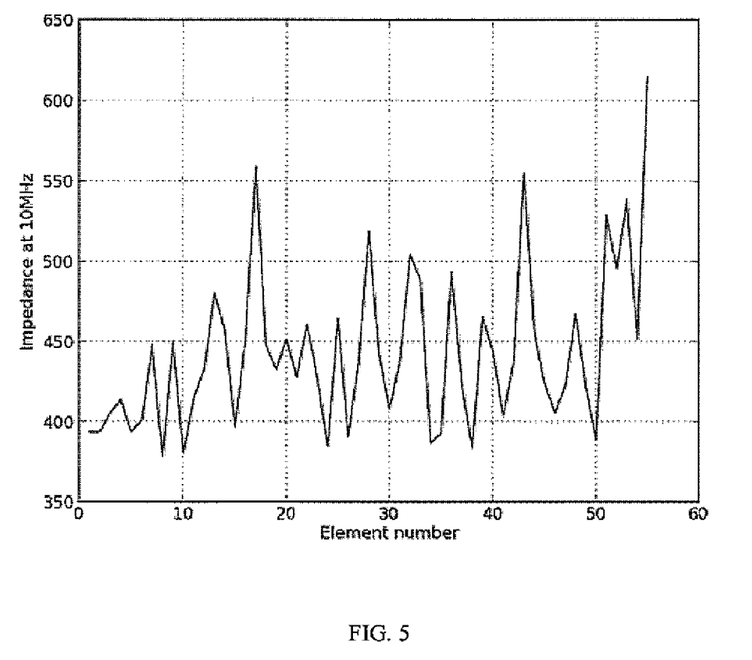
FIG. 5 shows a graph of impedance in ohms at 10 MHz vs array element number for the endoscope of the Example.

Measurements of the impedance of the elements (see FIG. 5) measured from the distal end of the flex circuit show that this technique does indeed provide a good electrical connection to the transducer elements, with low impedance electrical connections in the wire bond between the flex circuit and the array.

The invention claimed is:

1. An ultrasound device comprising:
   a transducer stack comprising:
      an array of ultrasound elements in electrical communication with a respective set of ultrasound array bonding pads;
      wherein the transducer stack comprises an ultrasound emitting surface and a plurality of side surfaces; and
   a printed circuit board, wherein an end portion of said printed circuit board is provided adjacent to a first side surface of said transducer stack, wherein an angle between the end portion of the printed circuit board and the ultrasound emitting surface is at least 60 degrees, and wherein said printed circuit board comprises a substrate comprising a plurality of conductive paths extending longitudinally therethrough;
   wherein an edge of said printed circuit board is positioned proximate to said ultrasound emitting surface; and
   wherein electrical connections are provided between said ultrasound array bonding pads and electrically conductive material exposed in said edge of said printed circuit board, such that each ultrasound element is electrically connected to a respective conductive path of said printed circuit board.

2. The ultrasound device according to claim 1 wherein the end portion of said printed circuit board is parallel to the first side surface of said transducer stack.

3. The ultrasound device according to claim 1 wherein the printed circuit board comprises:
   a linear array of vias formed within said substrate at an end of said substrate, such that the vias intersect respective electrically conductive paths within said substrate;
   wherein said vias are filled with electrically conductive material;
   wherein said vias are exposed in an edge of said substrate, forming a plurality of lateral bonding pads in said edge; and
   wherein electrical connections are provided between said lateral bonding pads of said printed circuit board and said ultrasound array bonding pads.

4. The ultrasound device according to claim 3 wherein said printed circuit board is positioned relative to said transducer stack such that said lateral bonding pads are coplanar with said ultrasound array bonding pads.

5. The ultrasound device according to claim 3 wherein said printed circuit board is positioned relative to said transducer stack such that said lateral bonding pads are coplanar with said ultrasound emitting surface.

6. The ultrasound device according to claim 3 wherein the printed circuit board is adhered to the first side surface of the transducer stack.

7. The ultrasound device according to claim 3 wherein the printed circuit board is flexible.

8. The ultrasound device according to claim 3 wherein the printed circuit board is a first printed circuit board and the plurality of lateral bonding pads are a first plurality of lateral bonding pads, the ultrasound device further comprising a second printed circuit board comprising a second plurality of lateral bonding pads;
   wherein an end portion of said second printed circuit board is provided adjacent to a second side surface of said transducer stack, wherein an angle between the end portion of the second printed circuit board and the ultrasound emitting surface is at least 60 degrees;
   wherein an edge of said second printed circuit board is positioned proximate to said ultrasound emitting surface; and
   wherein electrical connections are provided between said second plurality of lateral bonding pads of said second printed circuit board and said ultrasound array bonding pads.

9. The ultrasound device according to claim 8 wherein said first printed circuit board and said second printed circuit board are provided on opposite sides of said transducer stack.

10. The ultrasound device according to claim 9 wherein said ultrasound array bonding pads comprise a first array of ultrasound bonding pads and a second array of ultrasound bonding pads;
    wherein said first array of ultrasound bonding pads is provided proximate to said first side surface and said second plurality of lateral bonding pads is provided proximate to said second side surface;
    wherein electrical connections between said first array of ultrasound bonding pads and said ultrasound array elements, and between said second plurality of lateral bonding pads and said ultrasound array elements, are spatially interleaved; and
    wherein said first plurality of lateral bonding pads are electrically connected to said first array of ultrasound bonding pads, and said second plurality of lateral bonding pads are connected to said second array of ultrasound bonding pads.

11. An ultrasound probe comprising an ultrasonic device according to claim 1.

* * * * *

UNITED STATES PATENT AND TRADEMARK OFFICE
CERTIFICATE OF CORRECTION

PATENT NO. : 10,149,660 B2
APPLICATION NO. : 14/420452
DATED : December 11, 2018
INVENTOR(S) : Bezanson et al.

It is certified that error appears in the above-identified patent and that said Letters Patent is hereby corrected as shown below:

On the Title Page

Under abstract "11 Claims, 5 Drawing Sheets" should read --18 Claims, 5 Drawing Sheets--

In the Claims

Column 6 Line 55 please add the following claims:

12. A method of electrically connecting an array of ultrasound elements, wherein the ultrasound elements are in electrical communication with a respective set of ultrasound array bonding pads, the method comprising:
   providing a circuit board comprising a substrate having a plurality of conductive paths extending longitudinally therethrough, the printed circuit board comprising an edge having electrically conductive material exposed therein, the electrically conductive material being in respective electrical communication with the conductive paths;
providing a transducer stack comprising an array of ultrasound elements in electrical communication with a respective set of ultrasound array bonding pads,
wherein the transducer stack comprises an ultrasound emitting surface and a plurality of side surfaces;
providing the printed circuit board such that an end portion thereof is adjacent to a first side surface of the transducer stack, and such that an angle between the printed circuit board and the ultrasound emitting surface of the transducer stack is at least 60 degrees, and such that the edge thereof is aligned with the top surface; and
forming electrical connections between the ultrasound array bonding pads and the electrically conductive material exposed in the edge of the printed circuit board such that each electrode is electrically connected to a respective conductive path of the printed circuit board.

13. The method according to claim 12 wherein the electrical connections are formed by wire bonding.

14. The method according to claim 12 wherein the electrical connections are formed by thin metal film or conductive epoxy.

Signed and Sealed this
Twenty-second Day of October, 2019

Andrei Iancu
*Director of the United States Patent and Trademark Office*

15. The method according to claim 12 wherein the printed circuit board is flexible.

16. The method according to claim 15 wherein the vias are partial vias.

17. The method according to claim 12 wherein the edge having electrical conductive material exposed therein is formed by cutting the printed circuit board transversely.

18. The method according to claim 17 wherein the following steps are performed prior to cutting the printed circuit board:
forming a linear array of vias within the printed circuit board, such that the vias intersect respective electrically conductive paths that extend longitudinally through the printed circuit board;
filling the vias with an electrically conductive material, thereby forming a linear array of filled vias within the printed circuit board;
wherein the printed circuit board is cut transversely through the set of filled vias to form the edge of the printed circuit board, such that the set of filled vias are cut to form a plurality of bonding pads and to expose the plurality of bonding pads at the edge, wherein the bonding pads are in electrical communication with respective signal wires within the printed circuit board; and
wherein the electrical connections are formed between the ultrasound array bonding pads and the bonding pads such that each electrode is electrically connected to a respective signal wire.

UNITED STATES PATENT AND TRADEMARK OFFICE
CERTIFICATE OF CORRECTION

PATENT NO.       : 10,149,660 B2
APPLICATION NO.  : 14/420452
DATED            : December 11, 2018
INVENTOR(S)      : Andre B. Bezanson et al.

It is certified that error appears in the above-identified patent and that said Letters Patent is hereby corrected as shown below:

On the Title Page

Replace the Title Page with the Attached Title Page

In the Claims

Please add the following claim:
19. The method according to claim 18 wherein the vias are arranged in two rows through the epth of the printed circuit board, wherein one row of vias extends through a plurality of top layers of the printed circuit board, and the other row of vias extends through a plurality of bottom layers of the printed circuit board, and wherein the vias in the two rows are spatially interleaved across the printed circuit board.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*

(12) United States Patent
Bezanson et al.

(10) Patent No.: US 10,149,660 B2
(45) Date of Patent: Dec. 11, 2018

(54) ULTRASOUND ENDOSCOPE AND METHODS OF MANUFACTURE THEREOF

(71) Applicant: DALHOUSIE UNIVERSITY, Halifax (CA)

(72) Inventors: Andre B. Bezanson, Halifax (CA); Robert B. A. Adamson, Halifax (CA); Jeremy A. Brown, Halifax (CA)

(73) Assignee: DALHOUSIE UNIVERSITY, Halifax, NS (CA)

( * ) Notice: Subject to any disclaimer, the term of this patent is extended or adjusted under 35 U.S.C. 154(b) by 804 days.

(21) Appl. No.: 14/420,452

(22) PCT Filed: Aug. 9, 2013

(86) PCT No.: PCT/CA2013/050613
§ 371 (c)(1),
(2) Date: Feb. 9, 2015

(87) PCT Pub. No.: WO2014/022938
PCT Pub. Date: Feb. 13, 2014

(65) Prior Publication Data
US 2015/0209005 A1 Jul. 30, 2015

Related U.S. Application Data

(60) Provisional application No. 61/681,320, filed on Aug. 9, 2012, provisional application No. 61/710,696, filed on Oct. 6, 2012.

(51) Int. Cl.
*H01L 41/09* (2006.01)
*A61B 8/12* (2006.01)
(Continued)

(52) U.S. Cl.
CPC .............. *A61B 8/12* (2013.01); *A61B 8/4488* (2013.01); *H05K 1/189* (2013.01); *H05K 3/403* (2013.01);
(Continued)

(58) Field of Classification Search
CPC ................................ A61B 8/12; A61B 8/4488
(Continued)

(56) References Cited

U.S. PATENT DOCUMENTS 5,427,106 A * 6/1995 Breimesser ............ H04R 17/00
310/326
5,559,388 A * 9/1996 Lorraine ................ B06B 1/0622
310/327
(Continued)

FOREIGN PATENT DOCUMENTS

JP 2002247696 8/2002
WO 2012075153 6/2012

OTHER PUBLICATIONS

Bezanson, A.; Adamson, R.; Brown, J.A., "Fabrication and performance of a miniaturized 64-element high-frequency endoscopic phased array," Ultrasonics, Ferroelectrics, and Frequency Control, IEEE Transactions on , vol. 61, No. 1, pp. 33,43, Jan. 2014.
(Continued)

*Primary Examiner* — Thomas Dougherty
(74) *Attorney, Agent, or Firm* — Hill & Schumacher (57) ABSTRACT

To address limitations of conventional transducers, a phased array transducer is provided with a form factor suitable o for packaging into, e.g., an endoscope. A method of manufacture of small packaging transducers is also provided, whereby the overall package size is reduced by electrically connecting signal wires to array electrodes at an angle approximately normal to the array surface, thus largely
(Continued)

eliminating the bend radius requirements of conventional printed circuit boards or flex circuits.

19 Claims, 5 Drawing Sheets

(51) Int. Cl.
 *A61B 8/00* (2006.01)
 *H05K 1/18* (2006.01)
 *H05K 3/40* (2006.01)
 *H05K 3/00* (2006.01)
(52) U.S. Cl.
 CPC ..... *H05K 3/0052* (2013.01); *H05K 2203/049* (2013.01); *Y10T 29/49151* (2015.01); *Y10T 29/49165* (2015.01)
(58) Field of Classification Search
 USPC .......................................................... 310/334
 See application file for complete search history.

(56) References Cited

U.S. PATENT DOCUMENTS

| | | | |
|---|---|---|---|
| 5,810,009 A * | 9/1998 | Mine ............... | B06B 1/0622 310/334 |
| 5,857,974 A * | 1/1999 | Eberle ............. | A61B 1/0011 29/25.35 |
| 6,043,590 A * | 3/2000 | Gilmore .......... | B06B 1/0607 310/334 |
| 6,153,967 A * | 11/2000 | Kobayashi ...... | B06B 1/0622 310/327 |
| 6,541,896 B1 | 4/2003 | Piel, Jr. et al. | |
| 7,745,976 B2 * | 6/2010 | Cerofolini ...... | A61B 8/00 310/334 |
| 7,795,784 B2 * | 9/2010 | Davidsen ........ | B06B 1/0622 310/334 |
| 8,189,342 B2 | 5/2012 | Bang et al. | |
| 8,803,404 B2 * | 8/2014 | Kwon .............. | B06B 1/0622 29/594 |
| 2004/0095045 A1 | 5/2004 | Baumgartner | |
| 2007/0047377 A1 | 3/2007 | Bang et al. | |
| 2007/0222339 A1 | 9/2007 | Lukaes et al. | |
| 2008/0002375 A1 * | 1/2008 | Nozaki ........... | H05K 1/0266 361/749 |
| 2009/0034370 A1 * | 2/2009 | Guo ................. | B06B 1/0622 367/180 |
| 2009/0221873 A1 | 9/2009 | McGrath | |
| 2013/0100775 A1 * | 4/2013 | Spigelmyer .... | B06B 1/0607 367/137 |
| 2014/0350407 A1 * | 11/2014 | Chaggares ...... | B06B 1/0622 600/459 |

OTHER PUBLICATIONS

Latham, K.; Arthur, C.; Brown, J. "Broad-band, large delay range, high precision, and variable analog delay lines for a high-frequency phased array beamformer", Ultrasonics Symposium (IUS), 2014 IEEE International, On pp. 2197-2200.
Bezanson, A.; Leadbetter, J.; Brown, J.A. "Fabrication of a high-frequency phased array with sparse Vernier array element spacing for grating lobe suppression", Ultrasonics Symposium (IUS), 2014 IEEE International, On pp. 671-674.
Bezanson, A.; Adamson, R.; Brown, J.A., "Fabrication and performance of a miniaturized 64-element high-frequency endoscopic phased array," Ultrasonics Symposium (IUS), 2013 IEEE International , vol., No., pp. 765,768, Jul. 21-25, 2013.
Brown, J.A.; Leadbetter, J.; Leung, M.; Bezanson, A.; Adamson, R., "A low cost open source high frame-rate high-frequency imaging system," Ultrasonics Symposium (IUS), 2013 IEEE International , vol., No., pp. 549,552, Jul. 21-25, 2013.
J. M. Cannata, J. A. Williams, Q. Zhou, T. A. Ritter, and K. K. Shung, "Development of a 35-MHz piezo-composite ultrasound array for medical imaging," IEEE Trans. Ultrason. Ferroelectr. Freq. Control, vol. 53, No. 1, pp. 224-236, 2006.
J. A. Brown, F. S. Foster, A. Needles, E. Cherin, and G. R. Lockwood, "Fabrication and performance of a 40-MHz linear array based on a 1-3 composite with geometric elevation focusing," IEEE Trans. Ultrason. Ferroelectr. Freq. Control, vol. 54, No. 9, pp. 1888-1894, 2007.
J. M. Cannata, J. A. Williams, and K. K. Shung, "A kerfless 30 MHz linear ultrasonic array," in Proc. IEEE Ultrasonics Symp., 2005, vol. 1, pp. 109-112.
H.-C. Yang, J. Cannata, J. Williams, and K. K. Shung, "Crosstalk reduction for high-frequency linear-array ultrasound transducers using 1-3 piezocomposites with pseudo-random pillars," IEEE Trans. Ultrason. Ferroelectr. Freq. Control, vol. 59, No. 10, pp. 2312-2321, 2012.
J. M. Cannata, J. A. Williams, C. H. Hu, and K. K. Shung, "Development of high frequency linear arrays using interdigital bonded composites," in in Proc. IEEE Ultrasonics Symp., 2008, pp. 686-689.
M. Lukacs, J. Yin, G. Pang, R. C. Garcia, E. Cherin, R. Williams, J. Mehi, and F. S. Foster, "Performance and characterization of new micromachined high-frequency linear arrays," IEEE Trans. Ultrason. Ferroelectr. Freq. Control, vol. 53, No. 10, pp. 1719-1729, 2006.
Q . Zhou, D. Wu, C. Liu, B. Zhu, F. Djuth, and K. K. Shung, "Micro-machined high-frequency (80 MHz) PZT thick film linear arrays," IEEE Trans. Ultrason. Ferroelectr. Freq. Control, vol. 57, No. 10, pp. 2213-2220, 2010.
F. S. Foster, J. Mehi, M. Lukacs, D. Hirson, C. White, C. Chaggares, and A. Needles, "A new 15-50 MHz array-based micro-ultrasound scanner for preclinical imaging," Ultrasound Med. Biol., vol. 35, No. 10, pp. 1700-1708, Oct. 2009.
C . Hu, L. Zhang, J. M. Cannata, and K. K. Shung, "Development of a digital high frequency ultrasound array imaging system," in Proc. IEEE Int. Ultrasonics Symp., 2010, pp. 1972-1975.
L . Sun, W. D. Richard, J. M. Cannata, C. C. Feng, J. A. Johnson, J. T. Yen, and K. K. Shung, "A high-frame rate high-frequency ultrasonic system for cardiac imaging in mice," IEEE Trans. Ultrason. Ferroelectr. Freq. Control, vol. 54, No. 8, pp. 1648-1655, 2007.
Z. Torbatian, R. Adamson, M. Bance, and J. A. Brown, "A splitaperture transmit beamforming technique with phase coherence grating lobe suppression," IEEE Trans. Ultrason. Ferroelectr. Freq. Control, vol. 57, No. 11, pp. 2588-2595, 2010.
X. C. Jin, B. T. Ehuri-Yakub, F. L. Degertekin, I. Ladabaum, and S. Calmes, "Micromachined capacitive ultrasonic immersion transducer for medical imaging," in Proc. 20th Annu. Int. Conf. IEEE Engineering in Medicine and Biology Society, 1998, vol. 2, pp. 779-782.
I. O. Wygant, D. T. Yeh, X. Zhuang, S. Vaithilingam, A. Nikoozadeh, O. Oralkan, A. Sanli Ergun, G. G. Yaralioglu, and B. T. Khuri-Yakub, "Integrated ultrasound imaging systems based on capacitive micromachined ultrasonic transducer arrays," in IEEE Sensors, 2005, p. 704-707.
T. Pedersen, T. Zawada, K. Hansen, R. Lou-Moeller, and E. V. Thomsen, "Fabrication of high-frequency pMUT arrays on silicon substrates," IEEE Trans. Ultrason. Ferroelectr. Freq. Control, vol. 57, No. 6, pp. 1470-1477, 2010.
D. T. Yeh, O. Oralkan, A. S. Ergun, X. Zhuang, I. O. Wygant, and B. T. Khuri-Yakub, "High-frequency CMUT arrays for highresolution medical imaging," in Medical Imaging, 2005, pp. 87-98.
K. Midtbo, A. Ronnekleiv, K. A. Ingebrigtsen, J. Due-Hansen, E. Poppe, D. T. Wang, G. U. Jensen, and K. Schjolberg-Henriksen, "High-frequency CMUT arrays with phase-steering for in vivo ultrasound imaging," in IEEE Sensors, 2012, pp. 1-5.
D. T. Yeh, O. Oralkan, I. O. Wygant, A. S. Ergun, J. Wong, and B. T. Khuri-Yakub, "High-resolution imaging with high-frequency 1-D linear CMUT arrays," in IEEE Int. Ultrasonics Symp., 2005, pp. 665-668.
M. Zipparo, C. Oakley, R. Denny, S. Azim, V. Balannik, Z. Soferman, M. Berman, R. Nechushtai, and D. Kopelman, "3-D laparoscopic imaging," in IEEE Ultrasonics Symp., 2008, pp. 40-44.

(56) References Cited

OTHER PUBLICATIONS

D. T. Yeh, O. Oralkan, I. O. Wygant, M. O'Donnell, and B. T. Khuri-Yakub, "3-D ultrasound imaging using a forward-looking CMUT ring array for intravascular/intracardiac applications," IEEE Trans. Ultrason. Ferroelectr. Freq. Control, vol. 53, No. 6, pp. 1202-1211, 2006.

Z. Wang, W. Zhu, H. Zhu, J. Miao, C. Chao, C. Zhao, and O. K. Tan, "Fabrication and characterization of piezoelectric micromachined ultrasonic transducers with thick composite PZT films," IEEE Trans. Ultrason. Ferroelectr. Freq. Control, vol. 52, No. 12, pp. 2289-2297, 2005.

U. Demirci, A. S. Ergun, O. Oralkan, M. Karaman, and B. T. Khuri-Yakub, "Forward-viewing CMUT arrays for medical imaging," IEEE Trans. Ultrason. Ferroelectr. Freq. Control, vol. 51, No. 7, pp. 886-894, 2004.

PCT/CA2013/050613 International Search reported dated Oct. 28, 2013.

PCT/CA2013/050613 Written Opinion dated Oct. 28, 2013.

* cited by examiner